United States Patent [19]
Webb et al.

[11] Patent Number: 4,764,005
[45] Date of Patent: Aug. 16, 1988

[54] DOUBLE SCANNING OPTICAL APPARATUS

[75] Inventors: Robert H. Webb, Lincoln; George W. Hughes, Brookline, both of Mass.

[73] Assignee: Eye Research Institute of Retina Foundation, Boston, Mass.

[21] Appl. No.: 876,231

[22] Filed: Jun. 19, 1986

Related U.S. Application Data

[63] Continuation-in-part of Ser. No. 777,406, Sep. 17, 1985.

[51] Int. Cl.⁴ .................................................. A61B 3/10
[52] U.S. Cl. ...................................... 351/205; 351/221
[58] Field of Search ......................... 351/205, 211, 221

[56] References Cited

U.S. PATENT DOCUMENTS

| | | | |
|---|---|---|---|
| 4,213,678 | 7/1980 | Pomerantzeff | 351/7 |
| 4,579,430 | 4/1986 | Bille | 351/206 |

FOREIGN PATENT DOCUMENTS

| | | |
|---|---|---|
| 84402345.7 | 6/1985 | European Pat. Off. . |
| 85107359.3 | 1/1986 | European Pat. Off. . |
| 51-39959 | 10/1977 | Japan . |

OTHER PUBLICATIONS

Improved Imaging with the Scanning Laser Opthalmoscope, Robert H. Webb, George W. Hughes and Douglas P. Wornson, Winter 1985, Mar. 19–20, 1985 Opt. Assoc. of America Meeting.

Double Scanning and Eye Tracking with a Scanning Laser Ophthalmoscope, Robert H. Webb, George W. Hughes, Douglas P. Wornson, poster paper, ARVO meeting, Jun. 1985.

Manipulating Laser Light for Ophthalmology, Robert H. Webb, IEEE EMB Dec. 1985, pp. 12–16.

Flying Spot TV Ophthalmoscope, R. H. Webb, G. W. Hughes, and O. Pomerantzeff, Sep. 1980, vol. 19, No. 17/Applied Optics.

Scanning Laser Ophthalmoscope, Robert H. Webb and George W. Hughes, Jul. 1981, vol. BME-28, No. 7, IEEE Transactions on Biomedical Engineering.

Experimental Observations of the Depth-Discrimination Properties of Scanning Microscopes, D. K. Hamilton, T. Wilson, and C. J. R. Sheppard, Dec. 1981, vol. 6, No. 12/Optics Letters.

Scanning Laser Ophthalmoscopy, Martin A. Mainster, MD, PhD, George T. Timberlake, PhD., Robert H. Webb, PhD, George W. Hughes, ScD, vol. 89, No. 7, Jul. 1982—Ophthalmology.

Holographic Scanner, Glenn T. Sincerbox, Nov./Dec. 1982, Optic News.

Optics for Laser Rasters, Robert H. Webb, Applied Optics, vol. 23, No. 20/Oct. 15, 1984.

Retinal Localization of Scotomata by Scanning Laser Ophthalmoscopy, G. T. Timberlake, M. A. Mainster, R. H. Webb, G. W. Hughes & C. L. Tremp, Investigative Ophthalmology & Visual Science, vol. 22, pp. 91–97, Jan. 1982.

*Primary Examiner*—Rodney B. Bovernick
*Attorney, Agent, or Firm*—Lahive & Cockfield

[57] ABSTRACT

An optical instrument which operates with an incident optical beam scanned at high rates and with correspondingly small sized scanning devices, has a double-scanning optical system. The output reflected beam that is detected overfills the first-stage scanning element, yet the instrument attains a relatively high-contrast image. The instrument provides for astigmatism correction, graphic generation in the scanned beam, and the use of infrared wavelength laser beams as well as visible wavelength laser beams. It also provides for generating system timing pulses from a rotating scanning element.

6 Claims, 5 Drawing Sheets

DOUBLE SCANNING OPTICAL APPARATUS

The invention was made with the Government support under Grant No. R01EY05626 awarded by the National Eye Institute, Bethesda, Md. The Government has certain rights in the invention.

This application is a continuation-in-part of U.S. Application Ser. No. 777,406, filed Sept. 17, 1985.

FIELD OF THE INVENTION

This invention relates in general to optical instruments and methods, and more particularly to an instrument for scanning a surface or other structure with an optical beam, detecting the light emitted from the structure, and generating a two-dimensional representation of an image of the structure.

BACKGROUND OF THE INVENTION

In the art of optical instruments, it is known to scan a surface to be imaged with a small light source, collect the light reflected from the illuminated spot and direct it to a detector which provides an output signal varying in time in correlation with the scanning of the illuminated spot across the surface. The detector output can be stored in a permanent storage medium or provided directly to a scanning display device, such as a television raster or a cathode ray tube display. By synchronizing the scanning operation of the illuminating source with the scanning of the display signals, a two dimensional image is produced.

One such instrument is a scanning ophthalmoscope which produces an image of the fundus of the eye. It has been found that the use of a laser light source provides improved imaging in an ophthalmoscope. A laser scanning ophthalmoscope is described in U.S. Pat. No. 4,213,678. One problem associated with ophthalmoscopes of the type described in U.S. Pat. No. 4,213,678 is that the light collected, at the time the laser is illuminating a particular area on the retina, includes not only light reflected directly from that area, but also light scattered from other surfaces and materials within the eye. This scattered light can cloud or fog the image, since it represents light contributions from other than the specific illuminated area. In an ideal system, each small illuminated area of the target object being examined produces a corresponding image area in the output display, with a brightness or intensity related only to light reflected directly from that target area. In some situations, on the other hand, the scattered light by itself, to the degree that it can be separated from the light directly reflected from the iluminated target area, is useful for diagnostic purposes.

In a device as described in the noted patent, the entrance pupil for the scanning laser beam has a small cross sectional area within the pupil of the eye, typically 0.5 mm in diameter, whereas the exit aperture for the reflected light is the overall pupil of the eye, which typically is nine mm in diameter. The detector is placed in a plane conjugate to this exit aperture. In the embodiment described in the patent, the scanning is effected by deflection galvanometers. The horizontal galvanometer is driven at 15.75 kHz. in order to match the horizontal scan frequency of a conventional television sweep, which preferably is used to display the output image. The vertical galvanometer is driven at 60 Hz to produce 525 lines per frame of the output image, again corresponding to the generation of a conventional television raster.

In a scanning ophthalmoscope of this type, the resolution in the raster display of the retinal image directly corresponds to the cross sectional area of the laser spot as it scans the retina. The contrast of the ultimate image depends, at least in part, upon the proportion of light received by the detector which is directly reflected from the illuminated area. Thus, to the extent that scattered light indirectly reaches the detector at the same time as it receives the light directly reflected from the illuminated area, the image is fogged and the contrast is reduced. The term "reflected" is used herein in a broad sense to refer to all optical energy returned by the target structure, it hence includes returned optical energy that results from both specular and diffuse reflection.

One technique used in some optical instruments to improve contrast for images of this type may be termed double scanning. According to this technique, the optical system is arranged to provide that the light reflected from the illuminated target area is selected with a scanning-like action related to the scanning of the incident illumination in such a manner that, at a given instant, the reflected light received by the detector is only that which is reflected from the illuminated target area. In effect, as applied to an ophthalmoscope, the fundus conjugate plane thereby allowing discrimination, at the conjugate retinal plane, between the light directly reflected from the retinal locus and that scattered either anteriorly or positiorly, i.e. within the retina. This approach, however, has been deemed to be unsuitable for an instrument like the laser ophthalmoscope of the type described, because in that instrument the exit aperture for the reflected light is so large that the returning reflected beam was deemed to require an unduly large scanning element. Since, at the driving frequencies associated with a television raster, a deflection galvanometer is limited by mass considerations to a very small surface, in the order of three millimeters, a reflection galvanometer large enough to encompass the returning image has been deemed not feasible.

Another deflection element which has been used for scanning optical instruments is a multifaceted rotating polygon, which would have to rotate at sufficiently high speeds to produce a horizontal scan matching the television frequencies. However, once again the size of the facet required to encompass the image received from the eye's exit aperture is prohibitively large in terms of fabricating a polygonal reflector to rotate at the required speeds.

The acousto-optical deflector is also not available in a form considered suitable for the reflected beam in such an instrument, due to aperture limitations.

OBJECTS OF THE INVENTION

It accordingly is an object of the present invention to provide an optical system for producing a two-dimensional representation of the reflection characteristics of a scanned structure and having relatively high resolution and contrast.

Another object of the invention is to provide an optical instrument having double scanning, i.e. of both incident and reflected light, at high frequencies such as are conventional in a television-type raster display.

It is also an object to provide an ophthalmological instrument for providing a two-dimensional representation of reflection characteristics of structure within an eye essentially in response only to light reflected from the eye structure in a selected manner. In one particular embodiment, the image is created in response essentially to directly reflected light; an in another embodiment in response to indirectly reflected light.

It is another specific object of this invention to provide an ophthalmological instrument for providing a two-dimensional representation of the reflection characteristics of the fundus of an eye wherein the contrast of the ultimate image is enhanced by enabling essentially only directly reflected light to generate that image.

It is another object of the invention to provide a confocal scanning ophthalmoscope utilizing an infrared laser beam to scan the eye fundus.

It is still another object of the invention to provide a confocal scanning ophthalmoscope which produces a graphic image on the retina during the scan.

Other objects of the invention will in part be obvious and will in part appear hereinafter.

SUMMARY OF THE INVENTION

It has been found, in one practice, that a double scanning optical instrument can be constructed utilizing a laser source and a multifaceted polygonal reflector for horizontal scan, with a reflection galvonometer or other scanning element for vertical scan, where the facet size in the direction of scan for the polygonal reflector is necessarily small and the reflected beam from the exit aperture of the system is substantially larger than that facet dimension. In the illustrated embodiment described below, the small facets of the polygonal reflector intercept less than 20% of the reflected light from the exit aperture. However, unexpectedly, under these circumstances the instrument attains a significant improvement in contrast over a single scan system, despite the significant loss of throughput.

It has thus been found that an optical instrument, of the type which responds to light energy responsive to a scanned incident beam, can be provided with double scanning with at least one scan element having such a small size that the exit beam overfills it. That is, this scan element is of such small size that it intercepts only a portion of the exit beam. In spite of the resultant loss of exit beam energy, the double-scanning instrument attains images having significant improvements over those of prior instruments. An instrument according to the invention attains this improved performance even when configured to have a large optical exit aperture, as is often desired.

DESCRIPTION OF THE DRAWINGS

For a fuller understanding of the nature and objects of the invention, reference may be made to the following description and the accompanying drawing, in which.

DESCRIPTION OF THE PREFERRED EMBODIMENT

Figure 1:
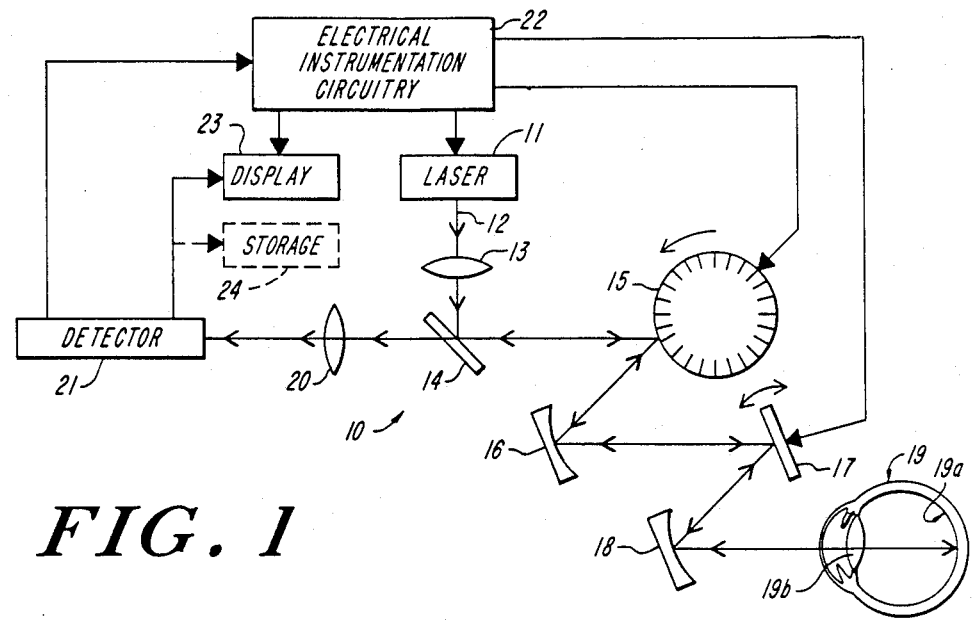
FIG. 1 is a diagrammatic representation of one embodiment of a scanning ophthalmoscope according to the invention.

FIG. 1 shows an embodiment of the invention in the form of an ophthalmoscope 10. A laser illumination source 11 produces a narrow incident light beam 12 which passes through a shaping lens system 13 which produces a slightly converging beam that impinges on a small turning mirror 14. The mirror 14 directs the incident laser beam onto facets of a multi-faceted rotating polygonal reflector scanner 15, which provides a horizontal scanning motion of the incident beam. The incident beam is reflected from this first stage scanning element onto a focusing mirror 16, which directs the beam onto the reflecting surface of a galvanometer reflector scanner 17 to produce a vertical scanning motion. From the galvanometer reflector scanner 17, which is a second stage scanning element, the laser input beam is directed onto a second focusing mirror 18, for focusing it onto the fundus 19a of the eye 19 of a subject. The incident beam enters the eye at the crystalline lens 19b.

The reflected light from the fundus 19 is directed back over a common portion of the foregoing optical input path, which includes focusing mirror 18, the second stage scanner 17, focusing mirror 16 and the first stage scanner 15. All of these common elements are mirrors and hence do not contribute reflections of the input beam back to the detector as noise background. The reflected output beam from the first stage scanner 15 in large part passes by the turning mirror 19 and hence separates from further traverse along the incident optical path. The output beam instead is directed through a focusing lens 20 and onto an optical detector 21.

The detector 21 is electrically connected to an electrical instrumentation unit 22 which provides electrical control signals to the laser source 11 and electrical drive signals to the scanning deflection elements 15 and 17. In essence, the instrumentation unit provides synchronization of the signals received at the scanning elements 15 and 17 so that the temporal order of the signals produced by the detector 21 can be correlated with the location of the scanned incident laser beam on the surface of the fundus. The control and synchronization which the instrumentation unit provides enables a two-dimensional display device 23, such as a television raster device, to form a two-dimensional display of an image of the eye fundus 19a, in response to the electrical signal which the detector produces in response to the reflected optical energy it receives. The detector signal may be applied to a long term storage element 24, such as a video tape recorder, for subsequent readout and display. For a description of a suitable electrical timing and control circuit, reference is made to U.S. Pat. No. 4,213,678 which is incorporated herein by reference.

THE LASER GENERATOR

The laser 11 can be any suitable laser light source which provides emission at frequencies yielding appropriate contrast for the fundus, or other target. Typically, the laser 11 is an Argon-Krypton laser or Helium-Neon laser operated at a power level to produce an illumination irradiance of one hundred microwatts per square centimeter at the fundus. The laser 11 may also be selected to emit in the infrared wavelength region to provide a scanning beam which does not require that the eye pupil be medically dilated to obtain an image of the fundus. For color imaging two lasers of different wavelengths may be employed and converted into a single beam with a dichroic beam splitter.

Figure 7:
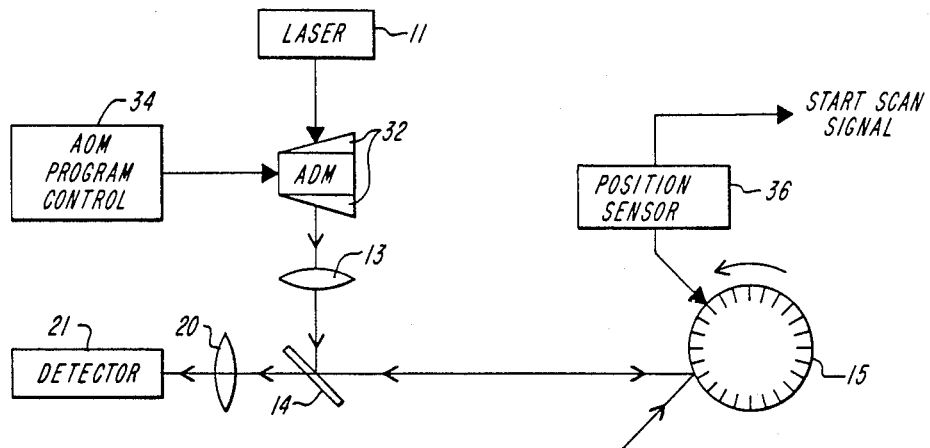
FIG. 7 is a diagrammatic representation of a modification to the embodiment of FIG. 1.

The laser beam, when it is emitting in the visible wavelength can also be arranged to present a graphic image, such as a cross in the scanning of the retina. FIG. 7 illustrates a modification to the embodiment of FIG. 1 in which additional elements are inserted between the laser 11 and the horizontal scanner 15. This embodiment includes an acousto-optic modulator (AOM) 30 for performing the graphic imaging function. The AOM receives a control input from a program control unit 34, which is typically a computer programmed to provide a signal timed to direct the laser beam emerging from the AOM away from the scanning path, thus blanking the scanning beam appropriately, to produce the image, a suitable computer being an IBM PC-XT made by International Business Machines, Yorktown Heights, N.Y. with a Revolution 512×8 graphics peripheral card with gen lock, made by Number Nine Computer, Cambridge, Mass. A program available for the graphic control is Media Cybeunetics' Halo, by Media Cybernetics of Takoma Park, Md.

A visible graphic image may also be provided when an infrared laser is employed, by utilizing an incandescent light beam incident on the AOM. The incandescent source will have sufficient intensity to stimulate the patient's retina but will not affect the scanned output image.

Prisms 32 are placed in the beam between the laser and the AOM and afer the AOM to allow lasers of different wavelength to be used, while preserving the same Bragg angle relationship for the different wavelengths within the AOM to maintain the output beams from the AOM on the same optical axis.

Figure 8:
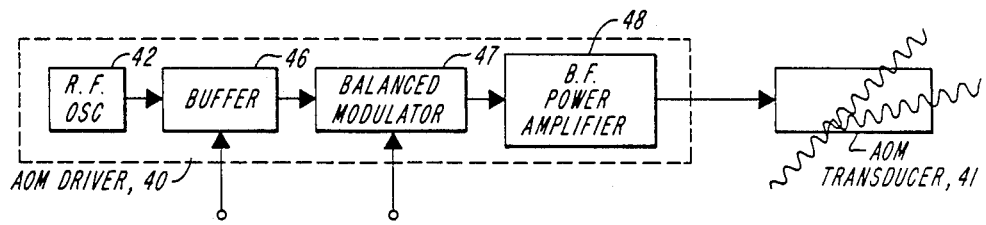
FIG. 8 is a block diagram of a portion of the ophthalmoscope of FIG. 7.

FIG. 8 is a block diagram of the acousto-optic modulator.

The acouto-optical modulator includes a driver unit 40 coupled to a transducer unit 41. The driver unit 40 includes an RF oscillator 42 typically operating at 40 MHz, followed by a buffer 46 which couples the oscillator to a balanced modulator 47. The output from the balance modulator 47 is coupled through an RF power amplifier 48 as the modulated RF output to the transducer element 41. The transducer element 41 is typically a glass crystal having Piezoelectric elements bonded to it to produce acoustic waves in the glass crystal. Optical waves incident on this crystal are then diffracted when the balanced modulator provides an output and remain undiffracted when there is no output from the balanced modulator, that is when the output from the driver 40 is blanked. The driver and transducer unit is commercially available from IntraAction Inc of Bellewood, Ill., under the trade designation AEM40 & MOP402B. In the conventional acousto-optic modulator a video input is provided to the balanced modulator 47 thus controlling the output signal to effect the optical modulation, control signals are applied to this input from the graphics program control. In this invention, however, a blanking input to the balanced modulator must be presented at times, not directly associated with the presentation of the graphics, in order completely to turn off the laser beam during the retrace of the display raster. This is done so that the laser beam does not impinge upon the patient's eye during this period, thus avoiding unnecessary irradiation of the patient's eye on distractingly visible retrace lines. This "absolute blanking" does not suffer from the requirement of careful adjustment typical of the balanced modulator circuit, but cannot achieve gray-scale modulation, since it is essentially on or off. In order to ensure that the inputs from the graphics control to the video input of the balanced modulator do not interfere with this retrace blanking, a retrace blanking signal is provided directly to buffer 46 to decouple the RF oscillator output 42 from the balanced modulator 47, thus disabling the driver unit 40 during this period.

The AOM diverts some of the beam energy into a first order (Bragg diffraction) beam at an angle typically about 15 mradians from the zero order beam. Either the original beam or the diffracted beam can be used to form the flying spot on the retina and its intensity is controllable over about three orders of magnitude by th AOM drive. The Bragg diffraction on which the modulation depends is from acoustic waves in a glass, of frequency 40 to 100 MHz. Two complications occur: because this is diffraction, it is inherently chromatic; and modulation of a high frequency carrier introduces other frequency components.

As above described the chromaticity is compensated with prisms 32 placed around the AOM. This brings both red an green beams to the glass at their preferred Bragg angles. The second prism is after the AOM to cause the beams to exit together, but the two prisms can be combined into one without serious problems. Minor adjustment at the combining dichroic beam splitter brings the two rasters into perfect alignment.

The trouble caused by the modulation itself is more subtle. When the RF carrier of, say, 40 MHz is turned off or on, lower frequencies are present for a few cycles. Lower frequencies deflect the beam at smaller angles, and a few cycles may well be a whole pixel. So, if the deflection is perpendicular to the fast (horizontal) scan direction, the beam moves off the raster line as it is turned off. In this orientation, all the line segments acquire little bends. This problem is solved if the AOM deflection angle is horizontal. The bends are still here, but they stretch the line segment out or tuck back into it, so that the only perception of them is that the leading edge of the segment is slightly softer and the trailing edge slightly sharper than expected.

THE INPUT OPTICAL SYSTEM

The purpose of the input optical system is to scan the fundus with a narrow optical beam to sequentially illuminate small segmental areas across the fundus surface in a known pattern so that the reflected light detected in time sequence can be electrically converted to a two-dimensional representation of the reflection characteristics of the fundus. In one illustrative instrument, the input optical system forms the incident laser beam with a cross sectional area of substantially 0.5 mm diameter at the entrance pupil of the eye and focussed on the fundus to produce a spot approximately twelve microns in diameter. The horizontal scanning motion in the illustrated preferred embodiment is provided by a rotational scanner which is shown in the preferred embodiment as a multi-faceted polygonal reflector scanner 15 which is rotated by an electric motor at speeds sufficient to produce a scanning frequency of 15.75 kHz to be compatible with a TV sweep frequency. A polygon of (m) facets turns the incident laser beam through a scan angle of 720/m degrees. Thus, if, for example, there are twenty-four facets on the polygon, it must rotate at 40,000 rpm in order to generate the 15.75 kHz scanning frequency. In order to rotate at this speed the moment of inertia of the polygon must be kept small. In one practical embodiment, each facet is six mm wide. The polygonal rotating reflector of the scanner 15 can be obtained commercially from Lincoln Laser (Phoenix, Ariz., No. PO-24 (A grade, G grade). A holographic disk scanner, scuh as made by Holotech, Inc., which has spaced holographic facets may be substituted for this polygon reflector. The scan angle can be changed optically by any of the subsequent optical elements. One approach to modifying the field of view is to set the vertical scanner to the same 28.8 degrees and then to modify the whole field of view at once. Resolution depends on the ratio of scan aperture to scan angle, so proper optical modification after the scan preserves the original resolution. With an input beam diameter of about 1 mm at the polygon, the available resolution is 794 spots, of which only 667 are used because of the 84% TV duty cycle. This is, in fact, about all that the available TV bandwidth can use. Once the resolution is fixed, at the polygon, the field of view can be increased or decreased by simple optical magnification. Increase of the field results in concurrent decrease of the beam diameter at the pupil, and this increases the spot size at the retina, so the resolution is unchanged.

Figure 10:
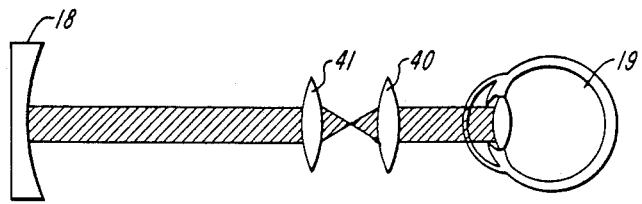
FIGS. 10 and 10a are diagrammatic representations of a telescope magnified for insertion in any of the embodiments illustrated.
Figure 10A:
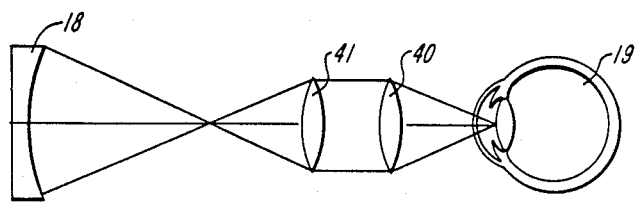

One method of changing the field size is to add an external telescope. This approach is illustrated in FIGS. 10 and 10a. FIG. 10 is an illustration of the beam diagram of this system while FIG. 10a illustrates the return reflection envelope. In FIG. 10 lenses 40 and 41, and are placed between the eye pupil and the mirror 18. Lens 40 is typically a 28-diopter ophthalmoscope lens and lens 41 may be a 14 diopter ophthalmoscope lens. By reversing the position of the lenses the field of view can be made smaller. If the distance between lenses 40 and 41 is adjusted to be unequal to the sum of the lenses' focal length, then refractive errors in the patient's eye can be compensated.

An advantage of this arrangement is that the telescope spacing adjusts beam focus, providing an independent compensation for patients' refractive error. This telescope system does however, produce reflections. Four refractive surfaces intercept the incoming laser beam and reflect it back to the detector. Some of these reflections can be blocked by appropriately placed stops and some can be diminished or displaced by suitable choice of surface bend and tilt. The residuum can at least be localized to one small area of the picture. Since it is a moving picture, the clinician can easily look around such a single reflection. Finally, in the tightly confocal arrangement (small aperture at the retinal conjugate), the reflections substantially vanish, so that it is only in the afocal mode that they are a problem.

Another method of changing field size avoids these problems: element 18 can be placed in a position to increse or decrease the field at the retina. This is inconvenient to implement, but is a preferred embodiment if reflections are a problem.

The vertical scanning motion in the illustrated preferred embodiment is introduced by a deflection galvanometer 17 that provides a scan action which corresponds with the television vertical scan of 60 Hz. Galvanometer controls, such as those manufactured by General Scanning of Watertown, Mass., are suitable for driving and controlling the position of the galvanometer mirror. The mirror 17 can, for example, be a type G120D General Scanning mirror.

With this structure and optical alignment in the instrument 10, the illustrated laser beam of 0.5 mm in diameter which it produces underfills each mirror facet of the polygon scanner 15, which, in the same illustrative embodiment, is six mm wide. The beam scanning pivots about a point in the plane of the eye's pupil.

The laser beam must be in focus at the retina, and the scan waist must be located (approximately) at the eyes of the pupil. Under these circumstances the spot size is appropriate for the available resolution, and the image will appear in focus at the TV screen even if it is not in focus at the confocal aperture. It is the focus of the incident beam which determines the picture's resolution and the focus of the return beam (at the confocal stop) which controls contrast. The fact that these controls are largely orthongonal is what allows flexibility as to mode of view.

The turning mirror 14 preferably is a stationary mirror reflector. It is small in size in order to produce a minimal shawdow in the output beam, and hence preferably is only large enough to intercept the input beam which the focusing element 13 directs, via the turning mirror, to the first stage scanner 15. In the configuration shown the turning mirror acts as the beam separator between the input and reflected return beam.

Figure 9:
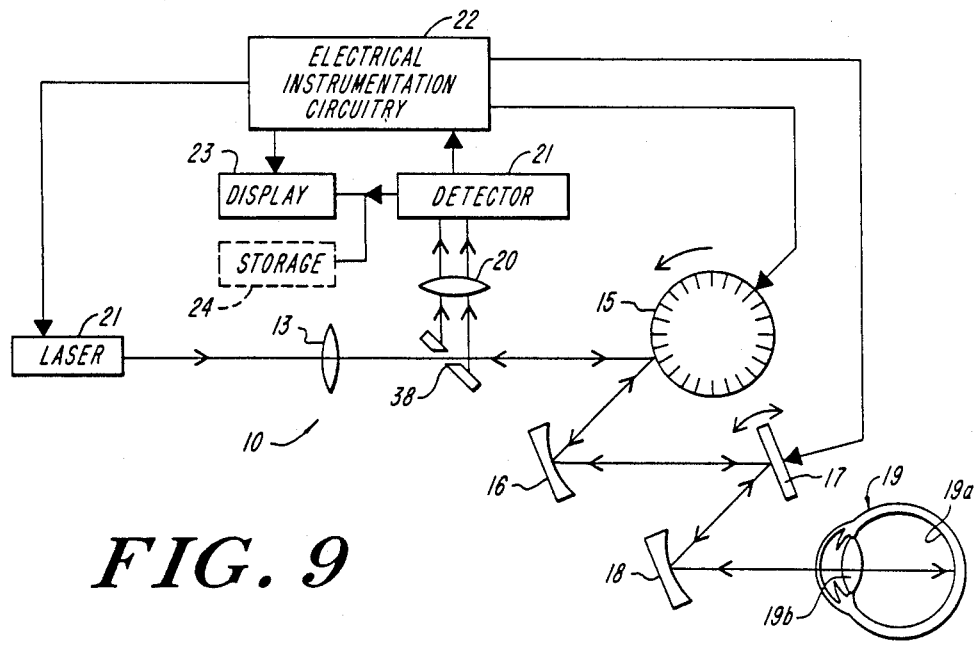
FIG. 9 is a diagrammatic representation of another embodiment of a scanning ophthalmoscope according to the invention.

In the embodiment illustrated in FIG. 9 the laser beam is originally directed toward the polygon scanner 15. A mirror 38 with a central hole allows the laser beam to pass through it. The return reflected beam from the scanner 15 is then reflected by the annular portion of mirror 38 to the detector 21.

Figure 2:
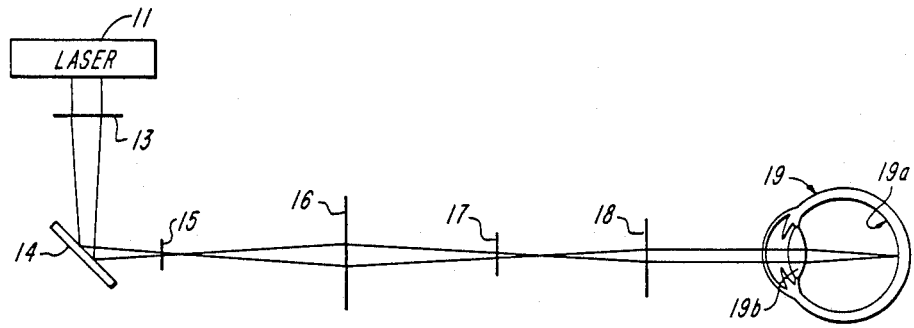
FIGS. 2 and 3 are explanatory ray diagrams of optical beam features of the embodiment illustrated in FIG. 1.
Figure 4:
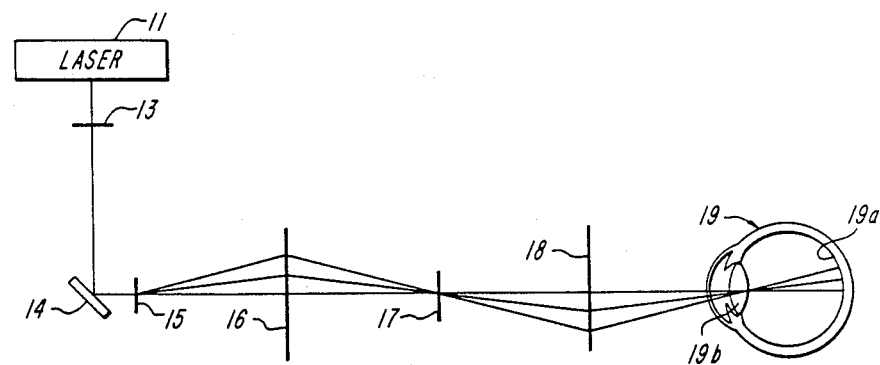
FIGS. 4 and 5 are explanatory ray diagrams of optical scan features of the embodiment of FIG. 1.

FIGS. 2 and 4 illustrate features of the input optical system. FIG. 2 represents the input beam with the scanners assumed to be stationary in a neutral, non-deflecting, position. The narrow collimated incident beam 12 from the laser is, in this partial representation, shaped by the optical elements 13, 14, 16 and 18, aside from the eye 19 of the subject. The incident beam is in focus at the retina 19a. The limiting aperture formed in this instance by the entrance pupil of the eye 19 is conjugate at the scanners 15 and 17.

FIG. 4, which represents scan features of the input system, illustrate the input beam instantaneously as a single ray which each scanning element moves, as a function of time. The drawing shows, in effect, a time exposure. In the illustrated envelope, the beams intersect at the scanners and their conjugates, which, for the scanned input beam includes the entrance pupil. The scan angle is the full angle of this envelope in the plane of the scan.

The mirror 18 is large and spherical. Large, so that even at f/2 (for the scan) the eye's pupil is far back from the optics. With human subjects there are some inflexible dimensions. The mirror is spherical because no aspheric is correct for both beam and scan systems at all points. That constraint can be understood by noting that the beam on one side of this mirror may be always collimated, no matter where it hits the mirror. So the mirror must have everywhere the same local curvature—which implies a sphere. Since the mirror is used off-axis, the scan system is then astigmatic.

The scan system astigmatism can be corrected by adjusting the separation between the horizontal and vertical scanners along the system's optic axis. The small spherical mirror 16 is used as a relay between the two scanners, for more flexibility. This mirror only focuses a line scan, so it can be tilted in the orthogonal plane, contributing no astigmatism. Both mirrors contribute coma, of course, so tilt angles are kept small.

THE OUTPUT OPTICAL SYSTEM

As noted, a major portion of the output optical system has a common optical path with the input system. This common path includes both of the scanning elements 15 and 17. In the illustrated instrument, it also includes the two focussing elements 16 and 18. However, in the output system, the light reflected from facets 15a of the rotating polygon scanner 15 passes around the turning mirror 14 and is incident on the detector optical system, which includes lens 20 and detector 21.

Figure 3:
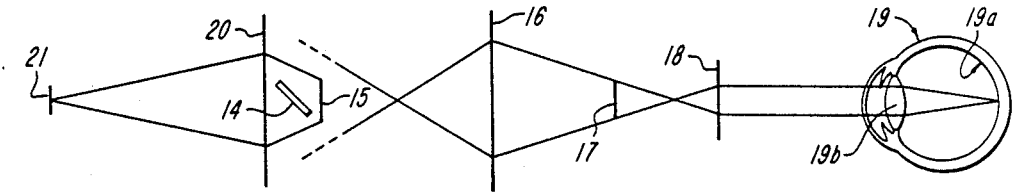

FIG. 3 represents the output beam without regard to the scanning elements 15 and 17, i.e. in the same manner as the representation in FIG. 2. As illustrated, the reflected beam from the fundus has an exit aperture large compared to the cross section of the scanning beam, preferably substantially the entire pupil of the eye, with a diameter of as much as nine mm. The image of this aperture at its conjugate plane also is nine mm. Absent magnification, the reflected output beam from the illuminated area on the fundus likewise is approximately nine mm in diameter at any conjugate of the exit pupil, which is where the scan elements 15 and 17 are located.

In this configuration the central region of the eye's pupil is used as an entrance pupil and the remaining annulus an exit pupil, thus conforming to Gulstrand's principle. This means that the scanners, optically conjugate to the pupil, need to be big enough to intercept that larger return beam. For the vertical scanner which moves as a 60 Hz sawtooth, a 10-15 mm mirror is suitable.

With the polygon, however, the available aperture (the facet) both rotates with respect to the beam and moves across it. The incident 1 mm beam and a 6 mm facet on the polygon combine to give just about the 84% duty cycle required for a TV raster. But the return beam may be as much as 15 mm in diameter, overfilling the facet even at the center of its sweep. This does lose light, but the facet is filled with signal light over most of its duty cycle, and therefore a very uniform fraction of the light from the annular exit pupil is recovered The ophthalmoscope 10 can have a small entrance pupil, as described above, due to the large radiance of the incident beam. The output beam, however, has relatively low radiance, and hence the provision of this large output pupil is desired to collect a maximal amount of output light energy. The large exit aperture hence enhances the high efficiency of the instrument. It also facilitates viewing a large portion of the eye fundus.

FIG. 3 also illustrates, with exaggerated scale, that the output beam passes around the turning mirror 14, which hence casts a small shadow generally of low significance.

It is desirable to separate the incident and return beams as close to the polygon facet as possible in order to place the incident beam in the center of the return beam and thus stop direct reflection from the cornea (and spectacles if desired) from reaching the detector.

Figure 5:
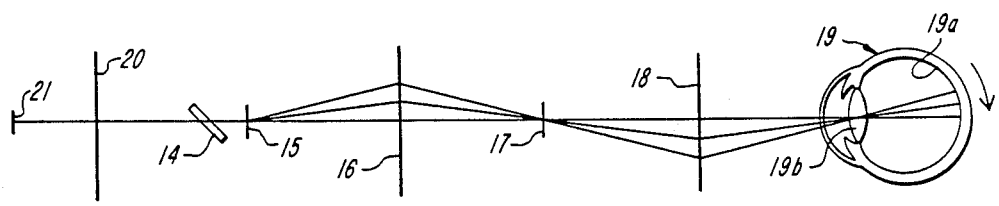

FIG. 5 represents scan aspects of the output beam, in the same manner as the scanned input beam representation in FIG. 4. The scanned output rays intersect, and the envelope of the scanned rays has minimal cross-section, at the pupilary plane of the eye 19 and at the scanning elements 15 and 17; this is the same as for the scanned input beam, FIG. 4. The former is at the plane of the exit pupil and the latter are at planes conjugate to it.

As also illustrated in FIG. 3, the relatively large cross-section of the output beam overfills each facet on the polygonal reflector scanner 15. With the six mm facet width of the illustrated embodiment, this overfill corresponds to a loss of throughput of approximately 80%. However, the reflected output light beam which the scanners 15 and 17 direct to the detector 21 is directly reflected substantially exclusively from the illuminated segmental area of the fundus. The detector 21 hence receives a minimal level of scatter or other unwanted light energy. These features enable the instrument to attain a resultant improvement of contrast at the detector which is unexpectedly high, and to yield a substantial improvement in contrast in the resultant image.

The placement in the instrument 10 of the detector 21 at the retinal conjugate plane, as apparent in FIG. 3, is advantageous because it allows the detector to have a small aperture. Optical detectors of this type have numerous advantages over large-aperture detectors. In particular, an avalanche diode detector detector 21 is highly suitable for use as the detector in this system.

Figure 6:
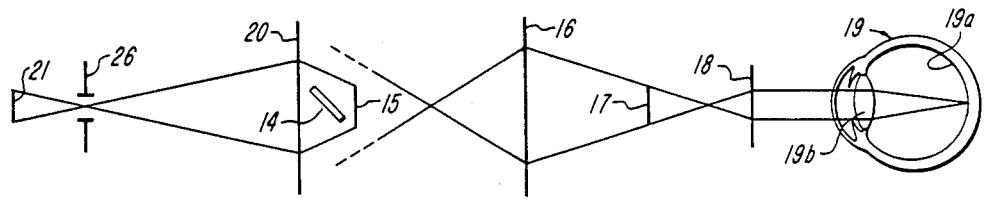
FIG. 6 is an explanatory ray diagram of the embodiment of FIG. 1, where the optical system includes a diaphragm stop and the detector is repositioned.
Figure 6A:
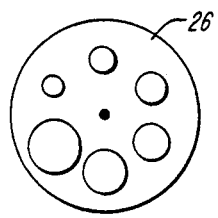
FIG. 6a is a view of the diaphragm stop of FIG. 6.

FIGS. 6 and 6A illustrate an alternative embodiment in which a diaphragm stop 26 is placed in the return beam path at the retinal conjugate plane and the detector 21 is moved to the pupillary conjugate plane. In FIG. 6 the envelope of the return beam is diagrammed. For convenience the diaphragm stop 26 can be formed as a disk with varying size openings (as illustrated in FIG. 6a) so that the size of the diaphragm stop 26 may be varied. Detectors are best placed at pupillary conjugates, since pupils tend to be about detector size (a few millimeters) while the retinal spot size is likely to be ten times smaller. In the invention described herein, the detector of choice is a semiconductor, typically a 1 mm avalanche diode with an integral amplifier such as RCA C30950E (RCA, Ste Anne de Bellvue, Quebec, Canada). When this detector is placed at the pupillary plane the retinal conjugate plane can be used for the placement of the aperture which limits the amount of retinal surface the detector receives light from. Since the retinal conjugate is a magnification (about ten times) of the retina a 1 mm aperture at the retinal plane restricts the retinal area seen to approximately 0.1 mm. On the other hand, if the aperture is made 10 mm, the retinal area seen is so much larger than the illuminating spot that the system is really afocal. A third option of invest is to use a 10 mm aperture with a central 1 mm stop, giving a "dark field" view of the retina, in which only light indirectly reflected is detected. With a rotatable aperture disk 26, as shown in FIG. 6a the view can be varied from tightly confocal to afocal or dark field. The same disk can be arranged to carry filters for various wavelengths. Following the retinal plane a simple 10X microscope objective (not shown) can be used to bring the pupil back down to 1 mm for a match to the avalanche diode.

If the polygonal reflector 15 is formed with twenty-five facets, distortions due to facet-to-facet and other variations remain stationary in the displayed raster image, since it is evenly divisable into 525 television lines. For this reason, it is deemed preferable that the polygonal sacnner have a number of reflective facets equal to an integral multiple of twenty-five. For different raster scan frequencies, a different number of facets would be appropriate. The controlling factor is that the number of reflecting facets should be integrally divisible into the number of raster lines. Further, as described above, there is a common optical path from the horizontal scanner 15 to the target object (in this example, the fundus of the eye) for the scanning beam and for the reflected light. Under these circumstances any reflection of the input laser beam from elements in the common optical path will appear as a noise signal to the detector. Accordingly the focusing elements 16 and 18, as well as scanning elements 15 and 17 are, front-surface mirrors.

While the instrument 10 has been described in terms of the advantages of de-scanning to produce signals corresponding only to light reflected directly from the illuminated target area, there are situations in which it is advantageous to look only at indirectly reflected light. This can be accomplished by moving the detector off the optical axis of the system to that it is in effect looking at target areas displaced from the direct illumination of the input beam. It has been found that information provided from these reflections also is useful in determining characteristics of an eye fundus. An alternative arrangement for attaining this response to only indirect illuminating is to image on the detect a target area concentric with, and larger than, the illuminated area, and to mask light reflected from the illuminated area, e.g. with a dark-field or central stop.

Moreover, if the detector is moved axially, the plane of the image can be moved to positions anterior to the retinal surface and thus various types of floaters, such as vitreous spots and strands may become visible in the image. Similarly, movement of the image plane to posterior, sub-surface positions enables the instrument to image interior structure of the eye fundus.

The 15.75 kHz horizontal scan frequency an the 60 Hz vertical scan frequency described above for the illustrated embodiment are for use with television standard adopted for the USA. These values can be selected to suit other standards in practice in other countries. For example, the standard which operates with 625 lines per frame, requires the same 15.75 kHz horizontal scan frequency and a 50.4 Hz vertical scan frequency.

Figure 11:
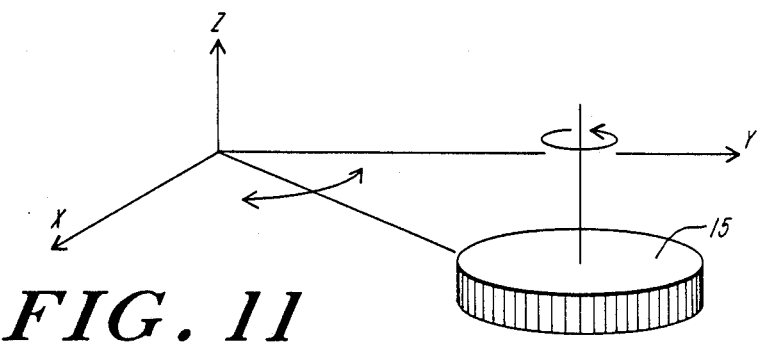
FIG. 11 is a diagram of the relationship between the axis of rotation of the scanning element of the embodiment of FIG. 1 and the allowable movement of the ophthalmoscope apparatus.

As a practical matter it is desirable to leave the patient confortably stationary (in a head rest) and for the physician to move the ophthamoscope to change the angle of the entrance beam. This means moving sources, detectors, optics and scanners. With a polygon rotating at 40,000, RPM gyroscopic considerations must be addressed. To avoid gyroscopic torques the polygon must be moved only parallel to or perpendicular to its axis of spin. In the present embodiment a conventional fundus camera mount is used to support the ophthalmoscope and its motion can be controlled over short distances by a joy stick. Since the mount translates the polygon along X, Y, or Z axes, and rotates it about the Z axis, as illustrated in FIG. 11, none of the motions tilt the spinning axis Z of the polygon 15 and consequently there are no gyroscopic torques on the bearings.

Figure 12:
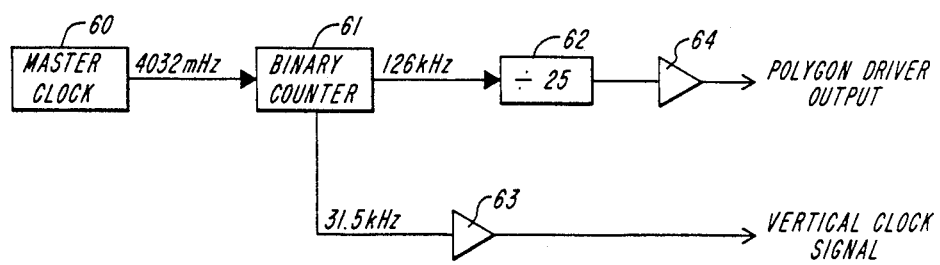
FIG. 12 is a block diagram of an electronic circuit employed in the practice of the invention.

In FIG. 12 there is illustrated an oscillator clock supply which provides a polygon driver output signal and a vertical clock output signal. The oscillator includes a crystal controlled master clock 60, typically operated at 4.032 mHz. The output of the clock 60 is provided to a binary counter 61 and a 126 kHz signal from the binary counter is provided to a divide by 25 circuit 62, the output of which provides the polygon driver output signal. A second signal is taken from binary counter 61 at 31.5 kHz and this is the vertical clock output signal.

Figure 13:
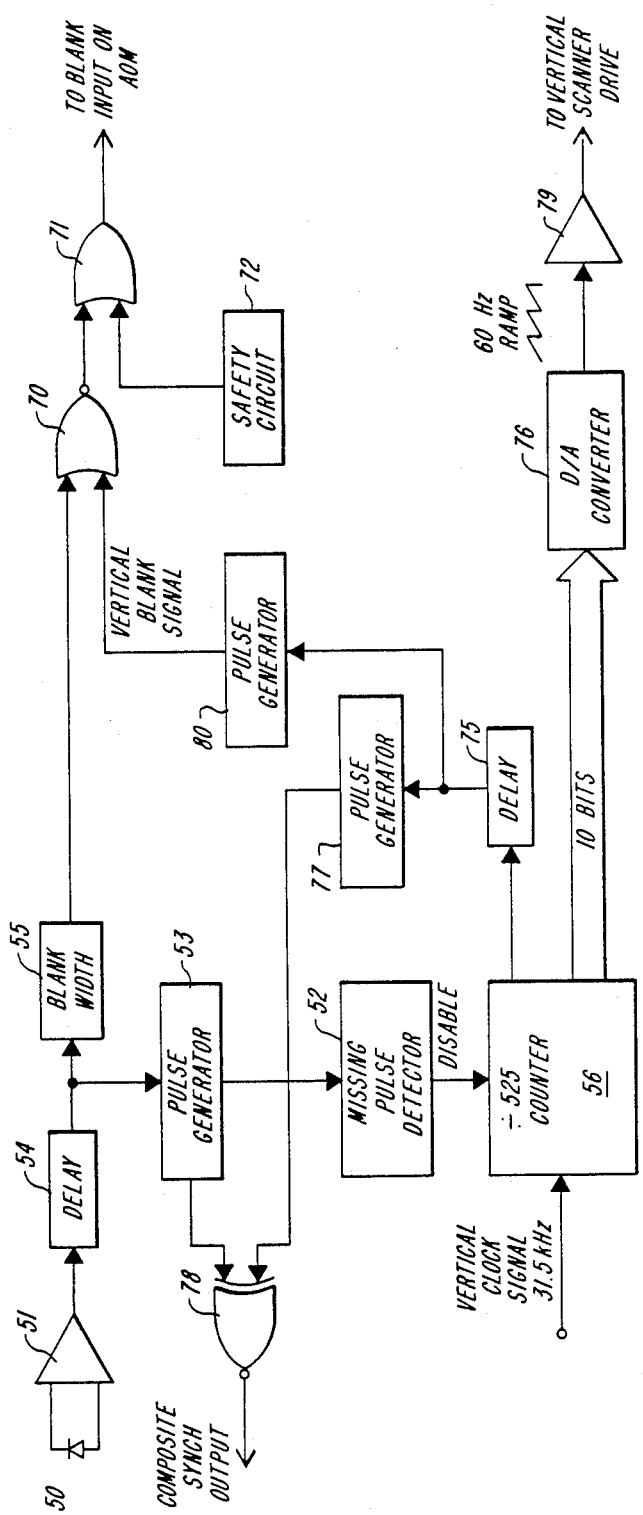
FIG. 13 is a block diagram of another electronic circuit employed in the practice of the invention.

FIG. 13 is a block diagram illustrating the manner in which the start of scan pulses generated from the pin diode 50 are processed to produce the blanking input for the AOM, the composite synch output for the monitor and other peripherals, and the vertical scanner drive. The output from the pin diode 50 is supplied through amplifier 51, delay circuit 54 and blank width control element 55 as one input to NOR gate 70. The delay unit 54 is arranged to equal the time required for the facet to rotate from the sensing position into the position where it intercepts the laser beam for scanning. Width circuit 55 provides for a pulse which is adjusted to be wide enough to cause blanking from the time one raster scan ends until the time the next raster scan is to begin. A second input to the NOR gate 70 is provided from the vertical synch signal. This signal is derived from counter 56 which is driven by the vertical clock signal. The vertical synch signal is processed through a delay unit 75 and a pulse generator 77. The output from NOR gate 70 is coupled through OR gate 71 to the blanking input on the AOM. A second input to the OR gate 71 is provided from a safety circuit 72. There are conventional safety circuits described in the literature, the purpose of which is to provide an output signal whenever a fault or failure in the overall ophthalmoscope is sensed. Thus, by coupling the safety circuit signal through the OR gate 71, it causes the laser beam to be diffracted away from the patient when such external faults occur.

The signal from delay 54 is provided to pulse generator 53, which has its output coupled to missing pulse detector 52. The latter circuit generates an output signal when there is no starter scan pulse. This output signal is provided as a disabling signal to counter 56.

Another output is taken from counter 56 to a digital to analog converter 76 which provides a 60 Hz ramp output signal to amplifier 79 to serve as a drive signal for the vertical scanning element. Thus the disabling signal to counter 56 insures that the vertical scanner is not operating when there is no start scan pulse detected, that is, when the polygon is not rotating at proper speed.

The output from pulse generator 53, together with the output from pulse generator 77 is provided to EXCLUSIVE OR gate 78 to produce an output designated "comp synch output". The comp synch output is provided as a synchronizing signal to the television monitor and similar peripheral devices. It is also provided as an output to the computer controlling the presentation of the graphics to time that unit in relation to the start scan signals.

While the invention has been described in terms of an ophthalmoscope embodiment, the same principles can apply to the imaging of reflection characteristics of planes and structures other than the fundus of an eye with enhancement of the contrast characteristics of the representation. Note that the optical system of an instrument according to the invention does not focus the image of the object being scanned to produce an output image, but rather converts a selected portion of the reflected light to a time varying electrical signal, which can then used to drive a synchronized imaging device and reproduce a representative visible image of the area being scanned.

Other embodiments of the invention including modifications of and deletions from this disclosed embodiment will accordingly be apparently to those skilled in the art and are within the scope of the following claims.

What is claimed as new and secured by Letters Patent is:

1. A scanning ophthalmoscope apparatus for providing a two-dimensional output representation of reflection characteristics of an eye fundus, said apparatus comprising
   a laser source for generating a laser beam of defined cross sectional area which is small compared to an area of the fundus which is to be scanned,
   an optical system for directing said laser beam through the pupil of the eye onto said fundus area, said optical system including a first scanning element comprising a rotating element having spaced facets for changing the direction of incident laser light and driving means for rotating said first scanning element to scan said laser beam along a first coordinate across an area of said fundus, said optical system including means for collecting light reflected from said scanned area and providing an exit aperture for the reflected light from said area and defined by the pupil of said eye, said optical system directing collected light back along the same optical path by which said laser beam was directed from said first scanning element onto said fundus, the cross sectional area of said collected light beam reflected from said fundus as it impinges upon said first scanning element being large compared to the dimension of facets of said first scanning element along the coordinate of scan, and
   detector means positioned to receive said reflected light from said first scanning element to generate a signal varying in time with the amount of light reflected from said first scanning element onto said detector means,
   display means for providing said two dimensional output representation of said eye fundus in response to said detector signal, and
   means for sensing the position of successive facets of the first scanning element and providing a position signal indicating the time when each successive facet occupies the same position, said position signal being provided to the display means to control the timing of horizontal lines produced on said display means.

2. A scanning ophthalmoscope apparatus for providing a two-dimensional output representation of reflection characteristics of an eye fundus, said apparatus comprising
   a laser source for generating a laser beam of defined cross sectional area which is small compared to an area of the fundus which is to be scanned,
   an optical system for directing said laser beam through the pupil of the eye onto said fundus area, said optical system including a first scanning element comprising a multi-faceted rotating polygonal reflector and driving means for rotating said first scanning element to scan said laser beam along a first coordinate across an area of said fundus, said optical system including means for collecting light reflected from said scanned area and providing an exit aperture for the reflected light from said area and defined by the pupil of said eye, said optical system directing collected light back along the same optical bath by which said laser beam was directed from said first scanning element onto said fundus, the cross sectional area of said collected light beam reflected from said fundus as it impinges upon said first scanning element being large compared to the dimension of facets of said first scanning element along the coordinate of scan, and
   detector means positioned to receive said reflected light from said first scanning element to generate a signal varying in time with the amount of light reflected from said first scanning element onto said detector means,
   display means for providing said two dimensional output representation of said eye fundus in response to said detector signal, and
   means for sensing the position of successive facets of the first scanning element and providing a position signal indicating the time when each successive facet occupies the same position, said position signal being provided to the display means to control the timing of horizontal lines produced on said display means.

3. Apparatus in accordance with either of claims 1 or 2 wherein said display means is a two-dimensional television type raster.

4. Apparatus in accordance with either of claims 1 or 2 and further including means for stopping said laser beam from scanning said eye fundus whenever a safety defect is sensed in said ophthalmoscope.

5. Apparatus in accordance with either of claims 1 or 2 and further including means for stopping said laser beam from scanning said eye fundus, and wherein said position signal is provided to said means for stopping said laser beam to stop said laser beam from scanning during the time when said horizontal trace is not displayed.

6. Apparatus in accordance with claim 4 wherein said means for stopping the laser beam scan is an acousto-optic modulator.

* * * * *